United States Patent [19]
Sanroma Virgili et al.

[11] Patent Number: 5,998,678
[45] Date of Patent: Dec. 7, 1999

[54] PROCESS FOR PREPARING CAROTENOID PIGMENTS

[75] Inventors: Nuria Sanroma Virgili; Joan Carles Ferrater Martorell; Mildred De Bloos De Clercq; Juan A. Fernandez Martin, all of Tarragona, Spain

[73] Assignee: Investigaciones Quimicas y Farmaceutics, S.A., Tarragona, Spain

[21] Appl. No.: 08/945,385

[22] PCT Filed: Feb. 25, 1997

[86] PCT No.: PCT/ES97/00049

§ 371 Date: Dec. 22, 1997

§ 102(e) Date: Dec. 22, 1997

[87] PCT Pub. No.: WO97/31894

PCT Pub. Date: Sep. 4, 1997

[51] Int. Cl.$^6$ .................................................. C07C 35/21
[52] U.S. Cl. ............................................................ 568/816
[58] Field of Search .............................................. 568/816

[56] References Cited

U.S. PATENT DOCUMENTS

| | | |
|---|---|---|
| 3,558,712 | 1/1971 | Surmatis . |
| 5,382,714 | 1/1995 | Khachik . |
| 5,523,494 | 6/1996 | Torres-Cardona . |
| 5,780,693 | 7/1998 | Bernhard .................................. 568/816 |

FOREIGN PATENT DOCUMENTS

WO96/02594 2/1996 WIPO .

OTHER PUBLICATIONS

Chem abs CA:101:210052 ab of Hua Hsueh 40 (4) pp. 109–111 by Yeh, 1982.
Chem abs CA:116:127815 ab of J Korean Chem Soc 36(1) pp. 165–166 by Kim, 1982.
Marusich et al., "Zeaxanthin As An Egg Yolk And Broiler Pigmenter", *Products and Technology—XV World Poultry Congress*, 310–312 (1974).
Marusich et al., "Zeaxanthin As A Broiler Pigmenter", *Poultry Science*, 55:1486–1494 (1976).
Andrews et al., "Carotenoids Of Higher Plants", *Acta Chem. Scand. B*, 24:139(1974).
Schiedt et al., "Absorption, Retention and Metabolic Transformations of Carotenoids in Rainbow Trout, Salmon and Chicken", *Pure and Appl. Chem.*, 685–692 (1985).
Karrer et al., "Conversion of α–carotene in to β–carotene and of xanthophyll into zeaxanthin", *Helv. Chim. Acta.*, 30:266 (1947).
Andrews et al., "Isomerization of ε–Carotene to β–Carotene and of Lutein to Zeaxanthin", *Acta Chem. Scand. B*, 24:137–138 (1974).
Sliwka et al., "Partial Syntheses of Diasteromeric Carotenols", *Acta Chem. Scand. B*, 518–525 (1987).
Maoka et al., "The First Isolation Of Enantiomeric And Meso–Zeaxanthin in Nature", *Comp. Biochem. Physiol.*, 83B(1):121–124 (1986).
Subagio et al., "Preparation of Lutein from Marigold Flowers and Esterification to Their Myristates", *Analytical Sciences*, 13:1025–1028 (1997).
Rüttimann et al., "Synthesis of Optically Active Natural Carotenoids and Structurally Related Compounds", *Helv. Chim. Acta,*63(6)1456–1462 (1980).
Englert et al., "Synthesis, Isolation, and Full Spectroscopic Characterization of Eleven (Z)–Isomers of (3R,3'R)–Zeaxanthin", *Helv. Chim. Acta*, 74:969–982 (1991).
Aasen et al., "Carotenoids of Flexibacteria", *Acta Chem. Scand. B,*26:404–405 (1972).
Abstract of Partali et al., "Enzymic resolution of zeaxanthin", *Biocatalysis*, 6(2):145–149 (1992).

*Primary Examiner*—Gary Geist
*Assistant Examiner*—Jean F Vollano
*Attorney, Agent, or Firm*—Burns, Doane, Swecker & Mathis, L.L.P.

[57] ABSTRACT

A process for the preparation of the carotenoid Zeaxanthin by isomerization and optional hydrolysis of a carotenoid precursor with an alkaline reagent in a polar organic solvent selected from the group consisting of an ether, polyhydroxyl alcohol, an ether-alcohol or a combination thereof. Also disclosed is a method of improving the pigment power of an oleoresin or vegetable extract by isomerizing and optionally simutanously saponifying the optically active carotenoids found therein by the action of an alkaline reagent in an organic medium; oxidizing the resulting optically active dihydroxycarotene and; reducing the resulting optically active keto product to generate the 3,3' dihydroxycarotenoid as a racemic mixture.

21 Claims, No Drawings

PROCESS FOR PREPARING CAROTENOID PIGMENTS

This application is the national phase of PCT/ES97/00049 filed Feb. 25, 1997 now, WO97/3189.

TECHNICAL SCOPE OF THE INVENTION

This report describes a new procedure for the preparation of formula I carotenoid (Scheme 1) and the pigments that have this compound as a basic component.

Scheme 1

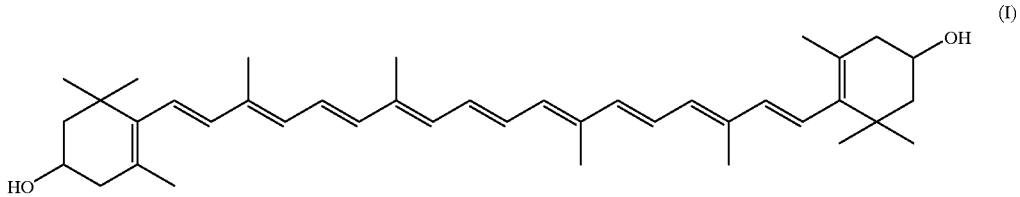

(I)

The objective that is proposed is, as described below, that of improving the pigmenting power of natural products obtained by extractive processes through the chemical transformation of one of their general formula II (Scheme 2) components in the formula I (Scheme 1) compound.

Chemical transformation of the general formula II compounds is also an objective of the present invention, when these do not come from a natural source but are obtained synthetically.

Scheme 2

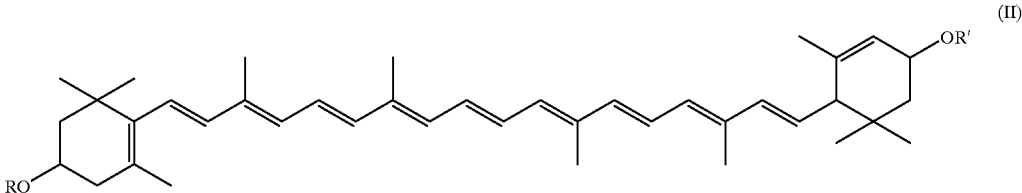

(II)

where R and R' are similar or different and may be H, lower acyl, fatty acyl or a hydroxyl protector group.

The name lower acyl refers to an acyl group with a branched or unbranched hydrocarbonated chain of 2 to 5 carbon atoms. The term fatty acyl refers to an acyl remainder coming from a fatty acid.

The compounds that are the subject of the present invention are part of a broad family of compounds called Carotenoids, within which are differentiated two big groups, the hydrocarbons or CAROTENES and their oxygenated by-products or XANTHOPHYLLS. The products herein described are part of this latter group.

The carotenoids are made up of eight isoprenoid units linked such that they are inverted in the exact center of the molecule, since the two central methyl groups remain in relative position 1,6, while the other non-terminal methyls remain in relative position 1,5.

All carotenoids can be derived formally from an acyclic $C_{40}H_{36}$ structure made up of a large central chain of conjugated double links, which was subjected to hydrogenation, dehydrogenation, cyclation, oxidation processes or a combination of the same.

Some carotenoids have a biological activity, such as provitamins A, that is, they generate "in vivo", through an enzymatic process, the respective vitamin A. This function is more common in those carotenes in which there is no substitution in the beta-ionone ring and, hence, they have a greater structural similarity with vitamin A. There are exceptions to this general rule and, thus, certain carotene epoxides have been described that have a high activity as provitamins.

However, most carotenoids do not have great activity as propharmacons and are therefore not useful as provitamins.

The extended conjugation of the double links that make up their hydrocarbonated structure give to the carotenoids a generally intense color, a quality for which they are highly valued, especially in the food industry.

The carotenoids are broadly distributed in nature, being responsible for the color of fruits, flowers and even birds and marine animals. They are produced by a multitude of plants and microorganisms. However, even though they can metabolize them, animals are not capable of synthesizing them Generally, they appear mixed among themselves, some or others predominating, depending on the natural source from where they come, and they customarily appear as the respective fatty acids.

OBJECTIVE OF THE INVENTION

One of the most broadly distributed xanthophylls in nature is Lutein (R=R=H. Scheme 2). This carotenoid is the main constituent of marigold resin (*Tagetes erecta L.*), an extractive product that constitutes one of the most important natural sources of xanthophyll. Together with Lutein, marigold resin has small quantities of other xanthophylls, mainly Zeaxanthin (I, Scheme 1).

The natural product has a high proportion of Lutein of around 85–90% as compared to a proportion of Zeaxanthin of around 4–5% of total xanthophylls.

An important number of pigmentation tests have been performed on chickens, eggs, . . . , comparing the pigmenting power of these two xanthophylls, lutein (or basically the extractive natural product from the marigold) and zeaxanthin (also of natural origin, from sources other than the marigold).

The result, as collected in *Proc. World's Poult. Congr.*, 15th of 1974 and in *Poult. Sci.*, 55, 1486 of 1976 indicates without a doubt that the pigmenting power of Zeaxanthin is approximately double that of Lutein.

As a consequence, based on the bibliographical antecedents described below, transformation of lutein from the extractive product in zeaxanthin with an isomerization process, which would translate into a very important improvement of the pigmenting power of the natural product, was proposed.

However, there is an extraordinarily important aspect that has to be considered, the stereo-chemistry of the products involved.

As indicated below, in reviewing the state of the art, direct racemization, that is, in only one phase, has many inconveniences, among others, the low yield obtained.

In this report, racemization of the isomerized product in a two-phase process is proposed The first consists of oxidation of the meso form of the Zeaxanthin to obtain the product 3-keto or 3-3'-diketo (III, Scheme 3) and the second, the reduction to obtain the racemic in one or in both positions (mixture 1:2:1 of the stereo-isomers 3R,3'R:3R,3'S (meso): 3S,3'S(I, Scheme 1)

Scheme 3

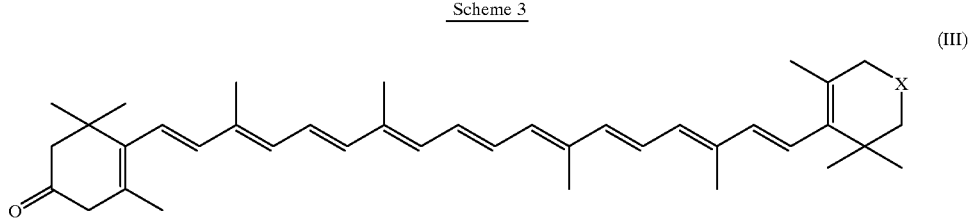

(III)

Lutein (R=R=H, Scheme 2) exhibits three chiral centers in its molecule so that, tentatively, there are several possible stereo-isomers. Andrewes et al, in their work "On the absolute configuration of Lutein" published in *Acta Chem. Scand B.*, 24, 139 (1974) showed that the absolute configuration of natural lutein, specifically that contained in marigold resin, is 3R,6R,3'R.

According to this information and given that the isomerization of lutein in zeaxanthin involves the disappearance of the chiral center in position 6 and does not alter any other, the end product should have the absolute configuration 3R,3'S, or meso form, optically inactive, as was confirmed by A. G. Andrewes in a work published in *Acta Chem. Scand. B.*, 137 (1974).

This aspect is of special importance if the studies published by K. Schiedt et al in the magazine *Pure and App. Chem.* in 1985 are considered. These authors made a comparative analysis of the pigmenting power of the various Zeaxanthin stereo-isomers.

The results indicate that, in the tested conditions, the stereo-isomer 3R,3'R is the one that has the greatest pigmenting power, 3R,3'S (meso) being the least effective. If an arbitrary value of 100 is assigned to stereo-isomer 3R,3'R, the meso form (or 3R,3'S) would have a value of 37 and the racemic one a value of 92.

Hence, the product obtained in the isomerization of natural Lutein in Zeaxanthin (isomer 3R,3'S) would in these cases have a pigmenting power even lower than natural Lutein itself, so that, instead of improving the coloring agent, the isomerization process would worsen it.

As a consequence of all this data and in order to achieve the objective of the present invention, that is, the improvement of the features of the natural product, the need to transform the isomerized product into an stereo-isomer of greater pigmenting power is proposed.

Hence, in the specific case of pigments in chickens, eggs and similar, the process must be completed with the preparation of the racemic mixture of the Zeaxanthin.

where X may be CHOH or C=O.

Within the scope of the present invention are also included the general II formula compounds (Scheme 2) that have been obtained in a way other than extraction from natural sources.

The stereo-isomerism of these can involve configurations other than those cited above, such as 3R,6R,3'R, whether pure stereo-isomers or mixtures among them, depending on the synthesis procedure used.

Hence, when isomerization is carried out on these compounds, resulting product I (Scheme 1) may be an stereo-isomer or a mixture of two or more, with a high pigmenting power.

In this case, the isomerization can increase sufficiently the pigmenting power of the starting product, so that a subsequent racemization would not be necessary.

STATE OF THE ART

Tests of the chemical transformation of a carotenoid in another that differs from the first one in the position of one of the double links of the cyclohexanic ring have been carried out through an isomerization process.

In *Helv. Chim. Acta*, 30, 266 (1947) is described the action of sodium on ethanol/benzene for the isomerization of alpha-carotene in beta-carotene and of xanthophyll. According to the experimental part of this article, the tests are performed starting with quantities of around 30 mg or carotenoid, and isolation and purification of the end products is done with chromatography.

In the same vein, Andrewes et al in *Acta Chem. Scand. B*, 2, 137 (1974) reported the isomerization of alpha-carotene and lutein with conversions of 16–21% and of 10–15%, respectively, using DMSO as a solvent and potassium methoxide as a reagent at 118° C. and in a closed vessel.

Both examples show usefulness at an analytical level, as the isomerization is done in order to confirm stereo-chemical aspects of the natural starting products.

More recently, and along the same vein, the process described in the patent PCT WO 96/02594 is noteworthy, in which process isomerization of Lutein from natural extracts is carried out in Zeaxanthin through the action of a very concentrated solution of alkali in water. In this procedure mention is made of the need for long periods of time, around 30 to 48 hours of reaction, to achieve conversions of around 15 to 20%.

Similar conditions are described in Mexican patent MEX 25952, which mentions the improvement of the natural product through an increase of the concentration of zeaxanthin through prolonged heating in an aqueous alkaline medium in a vacuum.

With respect to the racemization processes of chiral centers in xanthophylls, the state of the art includes a test of inversion of the configuration of the two chiral centers of the natural Zeaxanthin through the reaction of Mitsunobu. The results that were obtained, described by Liaaen-Jensen et al in *Acta Chem. Scanci. B,* 518 (1987) show a conversion of around 0.5–1% in inverted product Logically, in these conditions the process is not of industrial interest As for the oxidation-reduction processes, as a synthetic alternative of industrial interest, the information is scarce. Reactions of this type have been described only because of their analytical value in order to determine the relative proportions of the various stereo-isomers (See Matsuno et al, *Comp. Biochem. Physiol.,* vol 83B, 121 (1986)).

DETAILED DESCRIPTION

As described in the presentation of the objective, the development of the invention consists of three phases, the isomerization of the general formula II compounds (Scheme 2) in that corresponding to formula I (Scheme 1), oxidation for the preparation of the general formula III compounds (Scheme 3) and subsequent reduction to the racemic mixture.

The first phase of the procedure is based on the transformation of the II compounds (Scheme 2) into the respective I compound (Scheme 1) by action of a basic reagent in an organic medium.

It is important to point out that, as indicated above, the formula II compounds include the natural products, that is, those obtained through extractive processes and those that have been prepared by chemical synthesis.

The reagent that is used in the isomerization process is, as indicated, of basic nature. This term must be considered to include sodium and potassium hydroxides and alcoxides, earthy alkaline oxides, etc. With all of them a certain conversion has been obtained, in many cases achieving values of 90% or higher.

As to the quantity of the reagent, it has turned out to be a very important parameter for lowering the cost of the overall process, as high conversions have been achieved by using proportions of reagent in the order of from 1 to 40% of the starting product. An important piece of information is that in most cases the addition of an excess of reagent does not lead to an improvement in the isomerization results.

One of the most important aspects of the present invention is the nature of the solvent Thus, when in the description an organic medium is mentioned, it expressly refers to the use of organic solvents that may either be easily eliminated once the isomerization process is completed, through distillation, washing, filtration or drying, or else its elimination is not necessary because they are suitable as food additives.

Good results have been obtained with polar aprotic organic solvents of the ether, ester, ketone, . . . type. High conversions are also obtained by using alcohols, such as isopropanol tercbutanol, glycols, polyalcohols or mixtures among them as solvents.

The temperature is a very important parameter in development of the reaction. Excess heating leads to the formation of a large number of thermal degradation products and, hence, a great drop in the yield of the reaction. On the other hand, temperature values that are too low do not allow evolution of the starting products. It has been proven that the most suitable interval is between room temperature and 115° C., preferably between 65 and 90° C.

The temperature values in turn define the reaction time. This is another critical parameter, since, for a given temperature, excessively long periods of time do not increase the degree of conversion but instead favor the formation of many secondary products. The reaction times vary, depending on the conditions, between 5 minutes and 9 hours. Under optimum conditions, times of around 30 minutes are sufficient to achieve conversions of 80–90%.

At the industrial level, carrying out the reaction at atmospheric pressure involves a great simplification in the set-up and a reduction of the production costs. Under these conditions, and in an inert atmosphere, very good conversions and very pure products are obtained. However, as an alternative, the reaction can be carried out in a vacuum or in a closed pressurized reactor.

Once the isomerization reaction is completed, the end products are isolated and purified following customary methods. It should be pointed out that the high conversion achieved in the described conditions and the absence of significant amounts of impurities, together with the nature of the reagents and solvents that are used, allows carrying out the oxidation process without isolation of the isomerized product.

In the case, already considered, in which the R and/or R' remainders are hydroxyl protecting groups, the isomerization process carries with it the subsequent elimination of these groups through customary methods.

The second phase of the procedure of preparation of the coloring agent consists of oxidation of the hydroxyl groups of the I compound (Scheme 1) obtained through isomerization in order to obtain the respective keto groups (Scheme 3).

On this point, it is important to point out that oxidation can be done on one of the hydroxyl groups or on both, depending on the reaction conditions.

The reagents that are used to carry out this process can be chosen from among a broad variety of oxidizers, such as salts, oxides and Cr(VI) by-products, manganese oxides and by-products, DDQ, etc. . . . Good results have been obtained with chrome trioxide and its by-products in a neutral medium.

Given the characteristics of the products that are the subject of the present invention, the oxidation conditions must be extraordinarily soft. It is therefore important to carry out the oxidation reaction at low temperature, preferably between 0° and 15° C.

Under these conditions, reaction times of around 20 minutes to 3 hours are sufficient to complete the oxidation. It is not recommended that the reaction be prolonged excessively, since abundant degradation products would be generated that would lower the yield and make the purification process difficult The third and last phase consists of the reduction of the respective oxidation product (III, Scheme 3) in order to obtain the racemic (I, Scheme 1).

The reaction can be carried out on the isolated and purified product or else on the oxidation gross without prior isolation or purification.

Under these last conditions, an important aspect is the nature of the solvent, which must be suitable for oxidation, as well as for subsequent reduction. Good results have been obtained by using ethyl ether, dichloromethane or similar.

The reduction has been carried out by using different reagents, the best results being obtained with hydrides, such as sodium or potassium borohydride or aluminum alkyl hydrides.

The reduction times and conditions have been defined by the nature of the solvent and the reagent used. Good results have been obtained with reaction times of around 30 minutes by using potassium borohydride as a reagent in a mixture of methanol/dichloromethane at 0° C.

ADVANTAGES OF THE INVENTION

In the procedure herein described is proposed the preparation of carotenoid I (Scheme 1) and of pigments that have this compound as a basic component, with clear and important advantages as compared to the methods described in the bibliography.

In principle, it must be pointed out that this procedure will allow the transformation of compounds II (Scheme 2) in the corresponding I, both if one begins with pure products of natural or synthetic origin, as well as if the reaction is carried out on a mixture of these among themselves or with other coloring agents, as is the case with extractive products of natural origin (*Tagetes patula L. Tagetes erecta L.*)

As is evident in the examples on chemical isomerization of natural xanthophylls described in *Helv. Chim. Acta and Acta Chem. Scand.* mentioned above, the great limitation that the process has in the tested conditions is the low conversion that is achieved, due mainly to the formation of a large number of degradation products.

Together with the low yield that is achieved, these processes have the great inconvenience of being carried out in a medium that makes purification of the isomerized natural product difficult for its use as a food additive (dimethylsulfoxide).

This information means that, for these cases, the procedure is not useful at an industrial level, as it could not compete with other manufacturing alternatives, such as extraction from natural sources or total synthesis.

Recently, as indicated above, two methods isomerization of lutein of natural origin in zeaxanthin, contained in patents MEX 25952 and PCT WO 96/02594, through reaction with concentrated alkali in an aqueous medium have been described.

From the description gathered in both works can be concluded the low yield obtained (15–20%) after long reaction times (30–48 hours). Given the nature of the products involved, it is foreseeable that the attempts to increase the conversion by forcing the reaction conditions will lead to a significant increase in the degradation products with total xanthophyll loss.

In the method herein described, the problems associated with isomerization have been solved. Thus, the end products are prepared in very soft reaction conditions with an extraordinarily high conversion and with a very high degree of purity.

The reaction conditions allow achieving conversions of around 80–90% or higher, at the same time avoiding the formation of degradation products, that is, total loss of xanthophylls. A direct consequence is the possible direct use of the resulting product without prior isolation or purification.

An aspect of extraordinary interest of the present invention is that the isomerization reaction can be carried out in a suitable organic medium, such as a food additive, which, as applicable, will not be affected by the subsequent oxidation and reduction processes. Thus, and given the high conversion and purity that are obtained, it will be possible to use the isomerized product as an additive without subsequent manipulation.

The isomerization process involves an additional improvement to the characteristics of the product. Thus, it has been proven that the epoxides of the xanthophylls, products of little pigmenting value and hard to eliminate and that are always present in products of natural origin, disappear totally when the product is subjected to alkaline treatment in an organic medium. This aspect is a significant improvement to the quality of the end product At an industrial level and given what has been described, it is important to point out the simple set-up that is required to carry out the isomerization reaction. Thus, even though the present invention can be carried out in a vacuum or under low pressure, which cases are included in the subject of the invention, it is sufficient to use a reactor equipped solely with an efficient agitator.

One advantage, of extraordinary interest when work is done with extractive products, is that the isomerization can be carried out directly on the natural products themselves without prior saponification or purification.

As is known, the starting products that are the subject of this invention and that are of natural origin, usually show up in the form of fatty acid esters. Treatment of the same in the reaction conditions simultaneously produces saponification and the respective isomerization, which is a great innovation as compared to what has already been described.

Another important advantage of the procedure that is described herein is the lowering of cost that has been achieved in the overall process as compared to existing antecedents. Thus, aside from the already mentioned ease of set-up, the nature of the reagents and the reaction conditions and the method if isolation of the end products, contribute to lowering manufacturing costs and make this procedure a good alternative on an industrial scale.

The racemization of the end product, as has been described, is done in two phases, oxidation of the isomerized product and subsequent reduction.

The only bibliographical antecedents describe tests of direct inversion of the configuration with racemization, obtaining yields of around 0.5–1.0%.

Given these antecedents, the procedure herein described has clear advantages. Thus, according to the oxidation-reduction sequence, racemization is obtained with overall yields of over 80%. This result alone is already advantageous as compared to what is described in the bibliography.

However, to the information on the yield must be added the fact that, given the reaction conditions described above, the process can be performed without isolation of the intermediate product of the oxidation, which simplifies considerably the manipulation.

Final purification is done through customary methods, and, given the near total absence of degradation products, it is simple.

Finally, as a summary, it must be pointed out that the most important innovation of the present invention is the overall process. Thus, for the first time is described a procedure that allows improvement of a natural carotenoid coloring agent through total chemical transformation of one or several of its components in others of greater pigmenting power. There is no patent or non-patent antecedent in the bibliography that has developed this complete scheme.

EXAMPLES

Following are described examples for carrying out the invention, none of which is limiting.

Example 1
Reaction of isomerization of technical Lutein.
Over a shaken mixture of:
- 25 g. of technical Lutein
- 25 ml. of dioxane is added at room temperature and in a nitrogen atmosphere:
- 7.5 g. of sodium methoxide Nitrogen is bubbled inside the reaction mass for 10 minutes, and with strong shaking, the temperature is increased until it reaches 80° C.

Under these conditions shaking is continued for 7 hours. The solvent is cooled and evaporated in a vacuum.

The residue is treated with water and partially neutralized with HCl, 2N. Purification of this allows isolating a dark, semi-solid oil with a Zeaxanthin content of 65% with respect to the total of Xanthophylls.

Example 2
Oxidation of technical Zeaxanthin.

The product of example 1 is dissolved in 50 ml. of dichloromethane

The solution is cooled until it reaches 0° C. and the following is added with heavy shaking:
- 5 g. of dry chrome trioxide.

The mixture is shaken at this temperature for 2 hours until it is established through CCF that all the starting product has disappeared.

The solution is filtered and washed thoroughly with brine and with water. It is dried over sodium sulfate and filtered.

The product thus obtained is used for the next phase.

Example 3
Preparation of racemic zeaxanthin.

Over the dichloromethane solution of example 2, cooled previously to −5° C., the following is added with heavy shaking:
- 2 g. of potassium borohydride
- 20 ml. of methanol The mixture is shaken for 15 minutes at that temperature. The following is then poured:
- 10 ml. of hydrochloric acid at 10% and the shaking is continued for 20 minutes.

It is decanted and the organic layer is washed with water, dry over sodium sulfate, and it is filtered Elimination of the solvent under vacuum allows isolating the technical racemic Zeaxanthin with a richness referenced to the total xanthophylls of over 70%.

The analysis with Circular Dichroism (Dicroismo Circular-DC) showed that the isolated product did not have optical activity, which corresponds with the racemic mixture.

The detailed description of the present invention having been made, the following claims are declared as new and of the invention itself.

We claim:

1. A process for the preparation of a carotenoid having the following formula I:

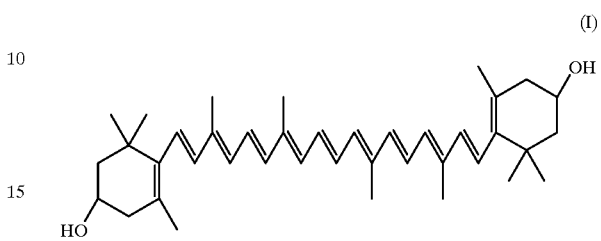

comprising treating a compound having the following formula II:

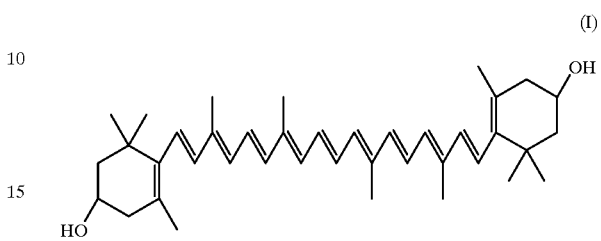

wherein R and R' are similar or different, and are hydrogen, lower alkyl, lower acyl, fatty acyl or a hydroxyl protector group, with an alkaline reagent in an organic medium, said organic medium comprising one or more polar organic solvents selected from the group consisting of an ether, a polyhydroxyl alcohol, an ether-alcohol or a combination thereof, and wherein said compound having the formula II is of natural or synthetic origin.

2. The process according to claim 1, wherein said alkaline reagent is a sodium alkoxide, a potassium alkoxide or a combination thereof.

3. The process according to claim 1, wherein said alkaline reagent is an alkali metal hydroxide, an alkaline earth metal hydroxide or a combination thereof.

4. The process according to claim 1, wherein said solvent is an ether.

5. The process according to claim 1, wherein said solvent is a glycol.

6. The process according to claim 1, wherein said solvent is a polyether-alcohol.

7. According to claim 1, wherein the temperature of the reaction is maintained between 15 and 115° C.

8. The process according to claim 1, wherein R and R' are hydrogen.

9. The process according to claim 1, wherein R and R' are a fatty acyl group.

10. The process according to claim 1, wherein the reaction is carried out at atmospheric pressure.

11. A method of improving the pigmenting power of an oleoresin or vegetable extract that contains as a basic component one or more carotenoids having the following formula II:

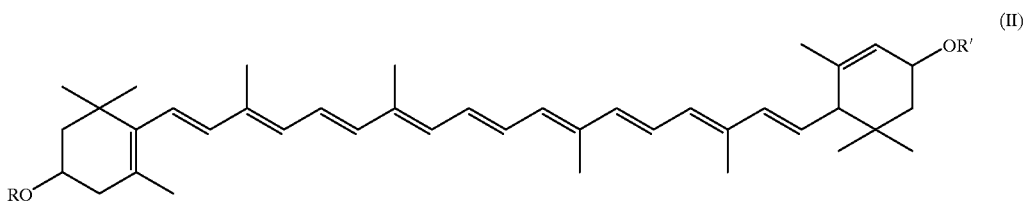

wherein R and R' are similar or different and, are hydrogen, lower acyl, fatty acyl or the a hydroxyl protector group; said method comprising isomerizing and, optionally simultaneously saponifying the corresponding optically active carotenoids through the action of an alkaline reagent in an organic medium, oxidizing the resulting optically active dihydroxycarotene and reducing the resulting 3,3'-diketocarotene to generate the 3,3'dihydroxycarotenoid as a racemic mixture.

12. The method according to claim 11, wherein the oxidation reaction is carried out with salts or oxides of chromium (VI).

13. The method according to claim 11, wherein the oxidation is carried out with manganese oxides in a neutral medium.

14. The method according to claim 11, wherein the reduction of the 3,3'-diketocarotene is carried out with hydrides.

15. The method according to claim 11, wherein R and R' are a fatty acyl group.

16. The method according to claim 11, wherein R and R' are hydrogen.

17. The method according to claim 11, wherein the three phases, isomerization, oxidation and reduction are carried out without isolation of the intermediate products.

18. The process according to claim 7, wherein the temperature of the reaction is maintained between 60 and 90° C.

19. A process for the preparation of a pigment containing a carotenoid having the following formula I

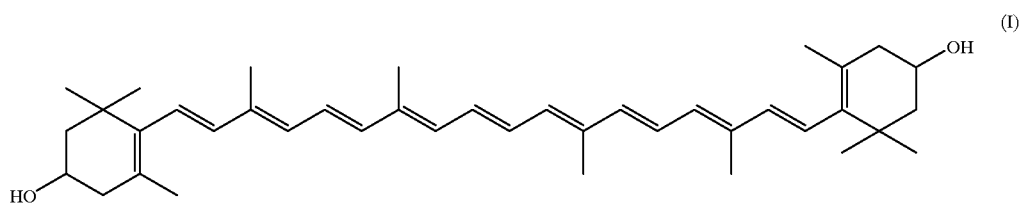

comprising treating an oleoresin or a vegetable extract containing a compound having the following formula II

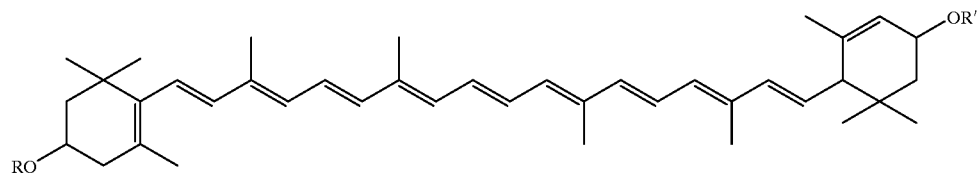

wherein R and R' are similar or different, and are hydrogen, lower alkyl, lower acyl, fatty acyl, or a hydroxyl protector group, with an alkaline reagent in an organic medium, said organic medium comprising one or more polar organic solvents selected from the group consisting of an ether, a polyhydroxyl alcohol, an ether-alcohol or a combination thereof.

20. The process according to claim 12, wherein the oxidation reaction is carried out with chrome trioxide.

21. The process according to claim 14, wherein the reduction of the 3,3'-diketocarotene is carried out with sodium or potassium borohydride.

* * * * *